(12) United States Patent
Kobayashi et al.

(10) Patent No.: US 11,583,483 B2
(45) Date of Patent: *Feb. 21, 2023

(54) HYDROGEN SUPPLY MATERIAL AND PRODUCTION THEREFOR, AND HYDROGEN SUPPLY METHOD

(71) Applicants: BOSQUET SILICON CORP., Osaka (JP); KIT Co., Ltd., Osaka (JP)

(72) Inventors: Hikaru Kobayashi, Kyoto (JP); Yuki Kobayashi, Kyoto (JP)

(73) Assignees: BOSQUET SILICON CORP., Osaka (JP); KIT Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/327,794

(22) PCT Filed: Jul. 27, 2017

(86) PCT No.: PCT/JP2017/027173
§ 371 (c)(1),
(2) Date: Feb. 22, 2019

(87) PCT Pub. No.: WO2018/037818
PCT Pub. Date: Mar. 1, 2018

(65) Prior Publication Data
US 2019/0231660 A1   Aug. 1, 2019

(30) Foreign Application Priority Data
Aug. 23, 2016 (JP) ............... JP2016-162520

(51) Int. Cl.
| | | |
|---|---|---|
| A61K 8/25 | (2006.01) |
| A61K 33/10 | (2006.01) |
| C11D 7/06 | (2006.01) |
| C01B 3/08 | (2006.01) |
| C01B 33/02 | (2006.01) |
| A61Q 19/10 | (2006.01) |
| A61K 33/00 | (2006.01) |
| A61Q 19/08 | (2006.01) |
| A61K 8/02 | (2006.01) |
| A61Q 7/00 | (2006.01) |

(52) U.S. Cl.
CPC .............. *A61K 8/25* (2013.01); *A61K 8/0241* (2013.01); *A61K 33/00* (2013.01); *A61K 33/10* (2013.01); *A61Q 7/00* (2013.01); *A61Q 19/08* (2013.01); *A61Q 19/10* (2013.01); *C01B 3/08* (2013.01); *C01B 33/02* (2013.01); *C11D 7/06* (2013.01); *A61K 2800/413* (2013.01)

(58) Field of Classification Search
None
See application file for complete search history.

(56) References Cited

U.S. PATENT DOCUMENTS

| | | | |
|---|---|---|---|
| 10,617,712 B2 | 4/2020 | Kobayashi et al. |
| 10,617,782 B2 | 4/2020 | Zhang et al. |
| 11,103,527 B2 | 8/2021 | Kobayashi et al. |
| 11,311,572 B2 | 4/2022 | Kobayashi et al. |
| 2003/0033991 A1* | 2/2003 | Cheng .................. C01B 3/08 123/3 |
| 2003/0059361 A1 | 3/2003 | Carberry |
| 2004/0067247 A1 | 4/2004 | De Sloovere et al. |
| 2005/0232837 A1 | 10/2005 | Troczynski et al. |
| 2009/0175985 A1 | 7/2009 | Canham |
| 2011/0311633 A1 | 12/2011 | Canham et al. |
| 2012/0034147 A1 | 2/2012 | Okita |
| 2012/0275981 A1 | 11/2012 | Foord et al. |
| 2012/0315684 A1 | 12/2012 | Hayashi et al. |
| 2013/0098250 A1 | 4/2013 | Satoh et al. |
| 2014/0377176 A1 | 12/2014 | Stephan et al. |
| 2015/0258136 A1 | 9/2015 | Lucas |
| 2016/0200571 A1 | 7/2016 | Kobayashi et al. |
| 2017/0333518 A1 | 11/2017 | Uekita et al. |
| 2019/0038664 A1 | 2/2019 | Kobayashi et al. |
| 2019/0216082 A1 | 7/2019 | Kobayashi et al. |
| 2020/0067554 A1 | 2/2020 | Kobayashi et al. |

FOREIGN PATENT DOCUMENTS

| | | |
|---|---|---|
| CN | 102227375 A | 10/2011 |
| CN | 102741172 A | 10/2012 |
| EP | 1220659 B1 | 9/2004 |
| EP | 1452484 A1 | 9/2004 |
| EP | 2630944 A1 | 8/2013 |
| JP | H0466189 U | 3/1992 |
| JP | 2004115349 A | 4/2004 |
| JP | 2006071330 A | 3/2006 |
| JP | 2006083078 A | 3/2006 |
| JP | 2007521244 A | 8/2007 |
| JP | 2007523096 A | 8/2007 |
| JP | 2008019115 A | 1/2008 |
| JP | 2008036530 A | 2/2008 |
| JP | 2008247839 A | 10/2008 |
| JP | 2009502157 A | 1/2009 |

(Continued)

OTHER PUBLICATIONS

English translation of Kita (WO/2016010139)(Apr. 26, 2020).*
English translation of WO/2017130709 (2021).*
English Translation of Notification of Reasons for Refusal received in JP Application No. 2019-131994 dated Aug. 13, 2019.

(Continued)

*Primary Examiner* — Patricia Duffy
*Assistant Examiner* — Garen Gotfredson
(74) *Attorney, Agent, or Firm* — Dorsey & Whitney LLP

(57) ABSTRACT

A layered solid formulation (100a) as one hydrogen supply material (200) according to the present invention includes silicon fine particles having a capability of generating hydrogen and aggregates of the silicon fine particles, and a physiologically acceptable medium (90b) that gets contact with the silicon fine particles or the aggregates thereof. The hydrogen supply material (200) is a hydrogen supply material for bringing the hydrogen into contact with the skin and/or the mucous membrane through the medium (90b).

6 Claims, 8 Drawing Sheets

(56) References Cited

FOREIGN PATENT DOCUMENTS

| | | |
|---|---|---|
| JP | 2009503128 A | 1/2009 |
| JP | 2010045204 A | 2/2010 |
| JP | 2010265158 A | 11/2010 |
| JP | 2011026211 A | 2/2011 |
| JP | 2011506279 A | 3/2011 |
| JP | 2011218340 A | 11/2011 |
| JP | 2011251873 A | 12/2011 |
| JP | 2013199413 A | 10/2013 |
| JP | 2013228319 A | 11/2013 |
| JP | 2014019689 A | 2/2014 |
| JP | 5514140 B2 | 4/2014 |
| JP | 2014084233 A | 5/2014 |
| JP | 2014193792 A | 10/2014 |
| JP | 2014205635 A | 10/2014 |
| JP | 2014227346 A | 12/2014 |
| JP | 2015113331 A | 6/2015 |
| JP | 2015531363 A | 11/2015 |
| JP | 2016001613 A | 1/2016 |
| JP | 2016152796 A | 8/2016 |
| JP | 2016155118 A | 9/2016 |
| JP | 2017104848 A | 6/2017 |
| JP | 6508664 B1 | 4/2019 |
| JP | 6592725 B2 | 10/2019 |
| KR | 10-1318939 | 10/2013 |
| KR | 101318939 B1 | 11/2013 |
| TW | I295935 B | 4/2008 |
| TW | 201126592 A | 8/2011 |
| TW | 201518206 A | 5/2015 |
| WO | 2005046707 A1 | 5/2005 |
| WO | 2005097670 A1 | 10/2005 |
| WO | 2009071219 A2 | 6/2009 |
| WO | 2010038064 A1 | 4/2010 |
| WO | 2012053472 A1 | 4/2012 |
| WO | 2014049677 A1 | 4/2014 |
| WO | 2015033815 A1 | 3/2015 |
| WO | WO2015033815 * | 3/2015 |
| WO | 2016010139 A1 | 1/2016 |
| WO | 2016129512 A1 | 8/2016 |
| WO | 2007026533 A1 | 3/2017 |
| WO | 2017130709 A1 | 8/2017 |

OTHER PUBLICATIONS

English Translation of Shinsuke Matsude, "Concentration of hydrogen molecules and splitting water using silicon nanoparticle," ISIR Osaka Univ., 2015.
Kentaro Imamura, et al, "Hydrogen generation from water using Si nanopowder fabricated from swarf", Journal of Nanoparticle Research, vol. 18, No. 5, 2016.
English Translation for Office Action dated Feb. 26, 2019 for Japanese application No. 2018-229323.
English Translation of Office Action dated Dec. 4, 2018 for Japanese application No. 2017-563788.
English Translation of Office Action dated Nov. 26, 2018 for Japanese application No. 2017-563788.
Matsuda, et al., "Concentration of Hydrogen Molecules and Splitting Water Using Silicon Nanoparticle", The 62nd JSAP Spring Meeting Koen Yokoshu, Mar. 2015.
Extended European Search Report for EP Application No. 17743940.3, dated Jul. 26, 2019.
Non-Final office action received in U.S. Appl. No. 16/073,305 dated Aug. 12, 2019.
"Mainly" Merriam-Webster.com. 2019. http://merriam-webster.com (Aug. 6, 2019).
English Translation of Notice of Reasons for Refusal received in JP Application No. 2018-535547 dated Jul. 9, 2019.
Bourzac, Katherine , "Hydrogen Fuel on Demand with Silicon Nanoparticles," Chemical & Engineering News (Jan. 24, 2013) https://cen.acs.org/content/cen/articles/91/web/2013/01/Hydrogen-Fuel-Demand-Silicon-Nanoparticles.html.
Loyless, Clay J. et al., "A Sodium Bicarbonate Dosing Methodology for pH Management in Freshwater-Recirculating Aquaculture Systems" 59 The Progressive Fish-Culturist 198-205 (1997).
Extended European Search Report received in EP App. No. 17843304.1 dated Feb. 7, 2020.
Extended European Search Report received in EP App. No. 17843305.8 dated Feb. 7, 2020.
English translation of PCT Publication No. WO 2015/033815 A1 retrieved Jul. 14, 2020.
English translation of CN Office Action for Application No. 201780008361.2, dated Apr. 26, 2020.
English translation of IN Office Action for Application No. 201827031149, dated Mar. 20, 2020.
English translation of Notice of Reasons for Refusal for JP Application No. 2017-135940, dated Jul. 14, 2020.
English translation for Office Action for TW Application No. 106125643, dated Oct. 6, 2020.
English translation of Office Action for CN Application No. 201780008361.2, dated Sep. 27, 2020.
English translation of Office Action for IN Application No. 201927007362, dated Nov. 17, 2020.
English translation of Office Action for IN Application No. 201927007363, dated Oct. 28, 2020.
English translation of Office Action for TW Application No. 106102324, dated Nov. 12, 2020.
English translation of Office Action for TW Application No. 106125642, dated Oct. 7, 2020.
English translation of Office Action for TW Application No. 106125644, dated Oct. 6, 2020.
Erogbogbo, Folarin et al., "On-Demand Hydrogen Generation Using Nanosilicon: Splitting Water Without Light, Heat, or Electricity", Nano Letters, vol. 13, published Jan. 14, 2013, pp. 451-456.
English translation of Office Action for TW Application No. 106125642, dated Jan. 5, 2021.
English translation for Office Action for JP Application No. 2019-034384, dated Dec. 15, 2020.
English translation of Office Action for IN Application No. 201927007366, dated Dec. 10, 2020.
Office Action for EP Application No. 17743940.3, dated Jan. 12, 2021.
Canham, L T. , "Nanoscale Semiconducting Silicon as a Nutritional Food Additive", Nanotechnology, vol. 18, No. 18, Apr. 2007.
Shabir, Qurrat et al., "Taste and Mouthfeel Assessment of Porour and Non-Porous Silicon Microparticles", Nanoscale Research Letters, vol. 7, No. 1, Jul. 20, 2012, pp. 1-6.
[English Translation] Brazilian Office Action dated Sep. 21, 2021 or Brazilian Application No. 112018015391-5.
[English Translation] Japanese Office Action dated Aug. 24, 2021 for Japanese Application No. 2021-063404.
[English Translation] Japanese Office Action dated Sep. 14, 2021 or Japanese Application No. 2019-034384.
[English Translation] Taiwanese Office Action dated Aug. 3, 2021 for Taiwanese Application No. 109140194.
[English Translation] Taiwanese Office Action dated Aug. 3, 2021 for Taiwanese Application No. 109140195.
[English Translation] Taiwanese Office Action dated Aug. 4, 2021 for Taiwanese Application No. 110102396.
[English Translation] Taiwanese Second Office Action dated Oct. 4, 2021 for Taiwanese Application No. 109140195.
English Translation for Office Action for JP Application No. 2019-181958, dated Jun. 2, 2021.
English translation of Hearing Notice for Indian Application No. 201827031149, dated Jun. 4, 2021.
English translation of Hearing Notice for Indian Application No. 201927007366, dated May 19, 2021.
English translation of Office Action for Chinese Application No. 201780051862.9, dated May 21, 2021.
English Translation of Office Action for Japanese Application No. 2018-535516, dated May 25, 2021.
English translation of Office Action for Japanese Application No. 2018-535548, dated Jun. 1, 2021.
English translation of Office Action for JP Application No. 2019-181957, dated Jun. 2, 2021.

(56) References Cited

OTHER PUBLICATIONS

"Bases—pH Values", obtained online via www.engineeringtoolbox. com, 2021.
"Medical Definition of Quasi", obtained online via www.medicinenet. com, 2021.
Erogbogbo, Folarin et al., Supporting Information of "On-Demand Hydrogen Generation Using Nanosilicon: Splitting Water Without Light, Heat, or Electricity", Nano Letters, vol. 13, published Jan. 14, 2013.
[English Translation] Final Notification of Reasons for Refusal dated Nov. 30, 2021 for Japanese Application No. 2021-063404.
[English Translation] Notification of Written Opinion on the First Examination dated Oct. 15, 2021 for Chinese Application No. 201780052364.4.
[English Translation] Notification of Written Opinion on the Second Examination dated Oct. 18, 2021 for Chinese Application No. 201780051862.9.
Final Rejection Action dated Nov. 15, 2021 for U.S. Appl. No. 16/327,782.
[English Translation] Chinese Office Action dated Mar. 11, 2022 for Chinese Patent Application No. 201780051862.9; pp. all.
[English Translation] Chinese Office Action dated Mar. 3, 2022 for Chinese Patent Application No. 201780051870.3; pp. all.
[English Translation] Final Notice of Reasons for Refusal dated Mar. 8, 2022 for Japanese Patent Application No. 2019-181958; pp. all.
[English Translation] Final Notification of Reasons for Refusal dated Feb. 15, 2022 for Japanese Patent Application No. 2018-535516; pp. all.
[English Translation] Taiwanese Office Action dated Jan. 6, 2022 for Taiwanese Patent Application No. 110104778; pp. all.
[English Translation] Taiwanese Office Action dated Jan. 17, 2022 for Taiwanese Patent Application No. 109140194; pp. all.
[English Translation] Taiwanese Office Action dated Jan. 17, 2022 for Taiwanese Patent Application No. 109140195; pp. all.
[English Translation] Taiwanese Office Action dated Jan. 17, 2022 for Taiwanese Patent Application No. 110131758; pp. all.
Hearing Notice dated Jan. 21, 2022 for Indian Patent Application No. 201927007362; pp. all.
U.S. Continuation U.S. Appl. No. 17/679,973 titled "Solid Preparation, Method for Producing Solid Preparation, and Method for Generating Hydrogen" filed Feb. 24, 2022; pp. all pages of application as filed.
[English Translation] Notice of Reasons for Refusal dated Jun. 7, 2022 for Japanese Patent Application No. 2021-066958; pp all.
[English Translation] 2nd Office Action dated Mar. 29, 2022 for Chinese Patent Application No. 201780052364.4; pp. all.
[English Translation] Notice of Reasons for Refusal dated Aug. 2, 2022 for Japanese Patent Application No. 2021-101920; pp. all.
[English Translation] The First Office Action dated Jul. 27, 2022 for Chinese Patent Application No. 202110564197.1; pp. all.
The Examination Report dated Aug. 22, 2022 for Indian Patent Application No. 202128007875; pp. all.
The Examination report dated Aug. 29, 2022 for Indian Patent Application No. 202128037822; pp. all.
The Examination report dated Aug. 29, 2022 for Indian Patent Application No. 202128037824; pp. all.
[English Translation] Taiwanese Office Action for Taiwanese Patent Application No. 111110405 dated Dec. 13, 2022, pp. all.
[English Abstract] Cheng, Ya-Yi, "Preparation and Characterization of Si and FeSi Nanoparticles", NCKU nstitutional Repository; Item 987654321/92947; [Department of Chemical Engineering] Dissertations and Theses, pp. all, Jun. 2009, 11 pages.
The Hearing Notice dated Dec. 13, 2022 for Indian Patent Application No. 201927007363, pp. all.
[English Translation] First Office Action for Chinese Patent Application No. 202110806702.9 dated Oct. 10, 2022, pp. all.
[English Translation] Notice of Reasons for Refusal for Japanese Patent Application No. 2021-182376 dated Oct. 24, 2022, pp all.
[English Translation] Second Office Action for Chinese Patent Application No. 201780051870.3 dated Sep. 15, 2022, pp. all.
[English Translation] Second Office Action for Chinese Patent Application No. 202110564197.1 dated Oct. 12, 2022, pp. all.
Communication Pursuant to Article 94(3) EPC for European Patent Application No. 17843305.8 dated Nov. 3, 2022, pp. all.
European Office Action for European Patent Application No. 17843304.1 dated Nov. 3, 2022, pp. all.
The Examination Report for Indian Patent Application No. 202128034241 dated Oct. 18, 2022, pp. all.

\* cited by examiner

[Fig.1]
(a)
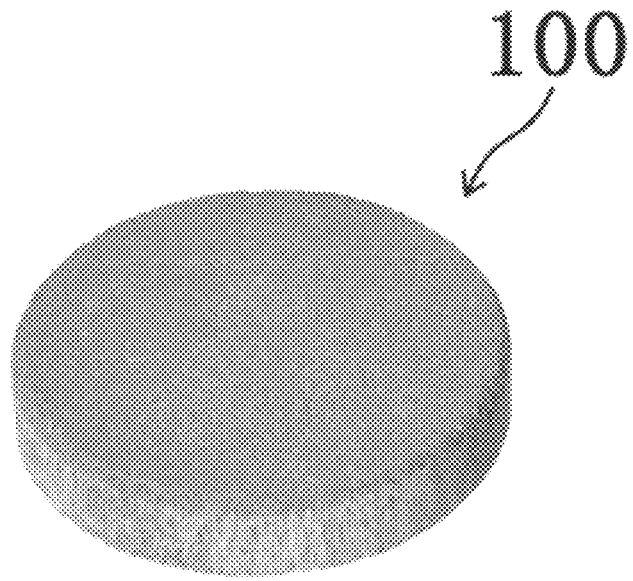
100
(b)
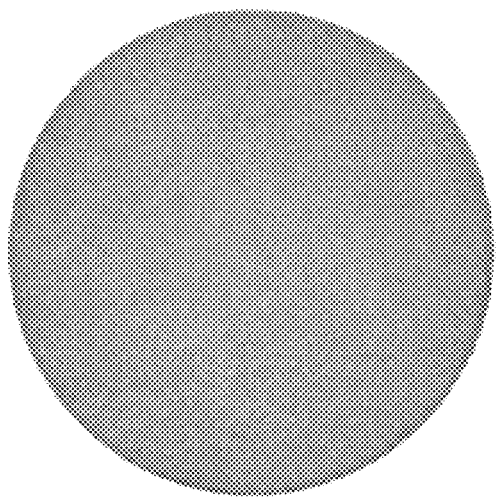

[Fig.2]
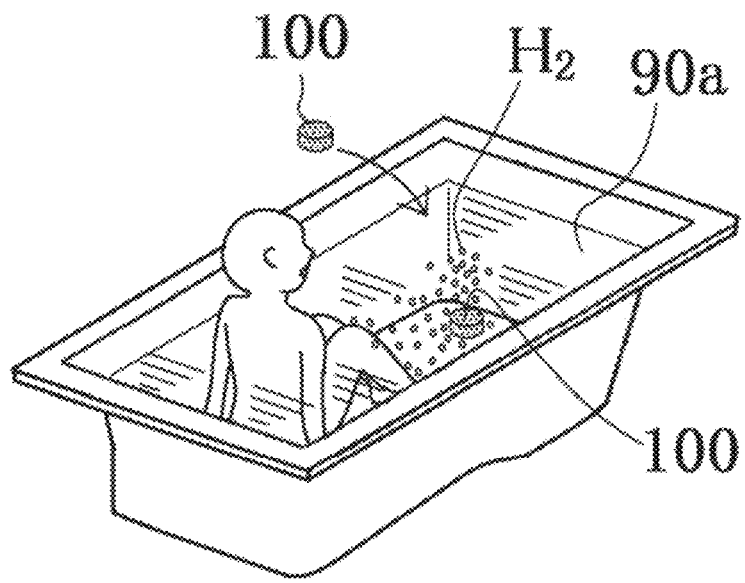
[Fig.3A]
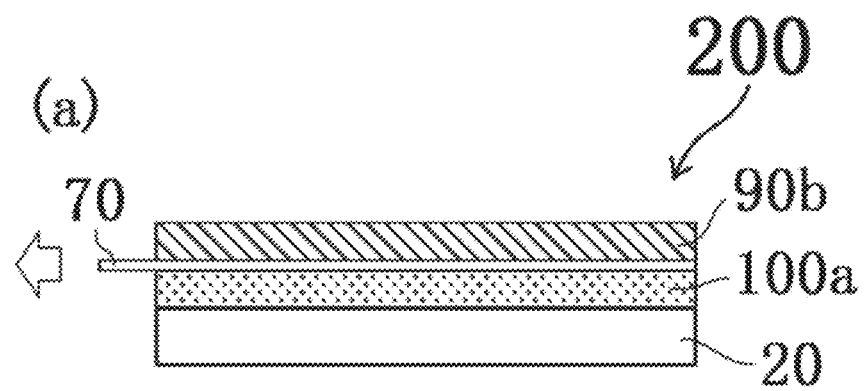
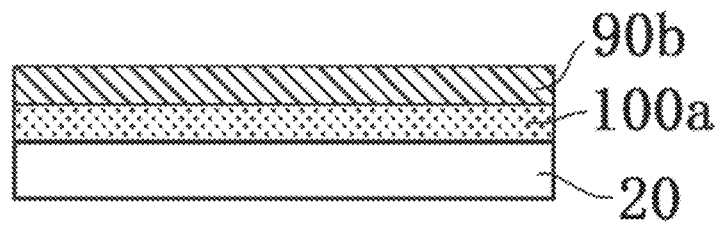

[Fig.3B]
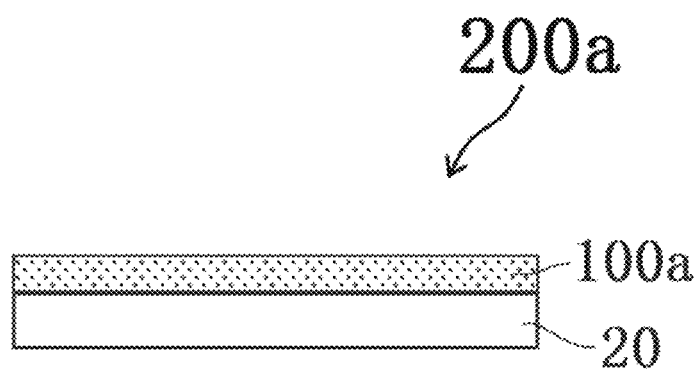
[Fig.4]
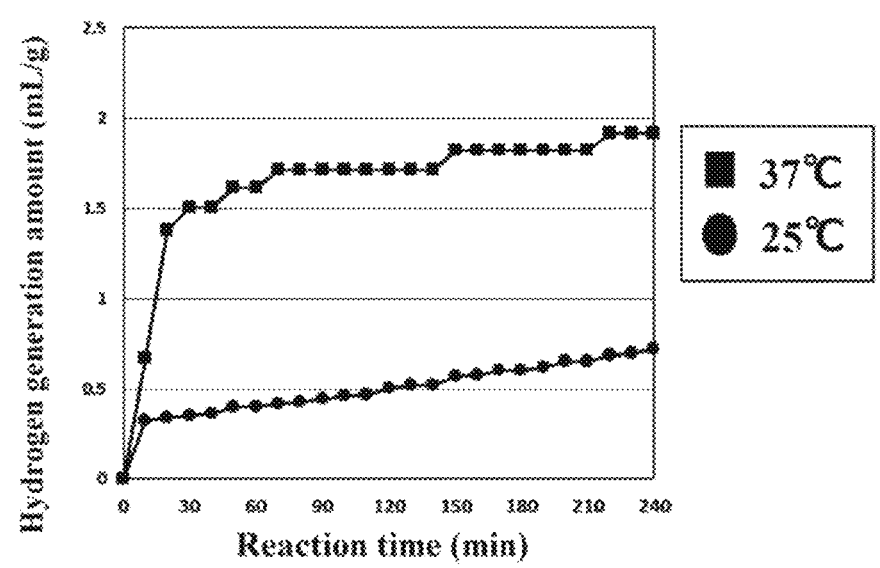

[Fig.5A]

[Fig.5B]
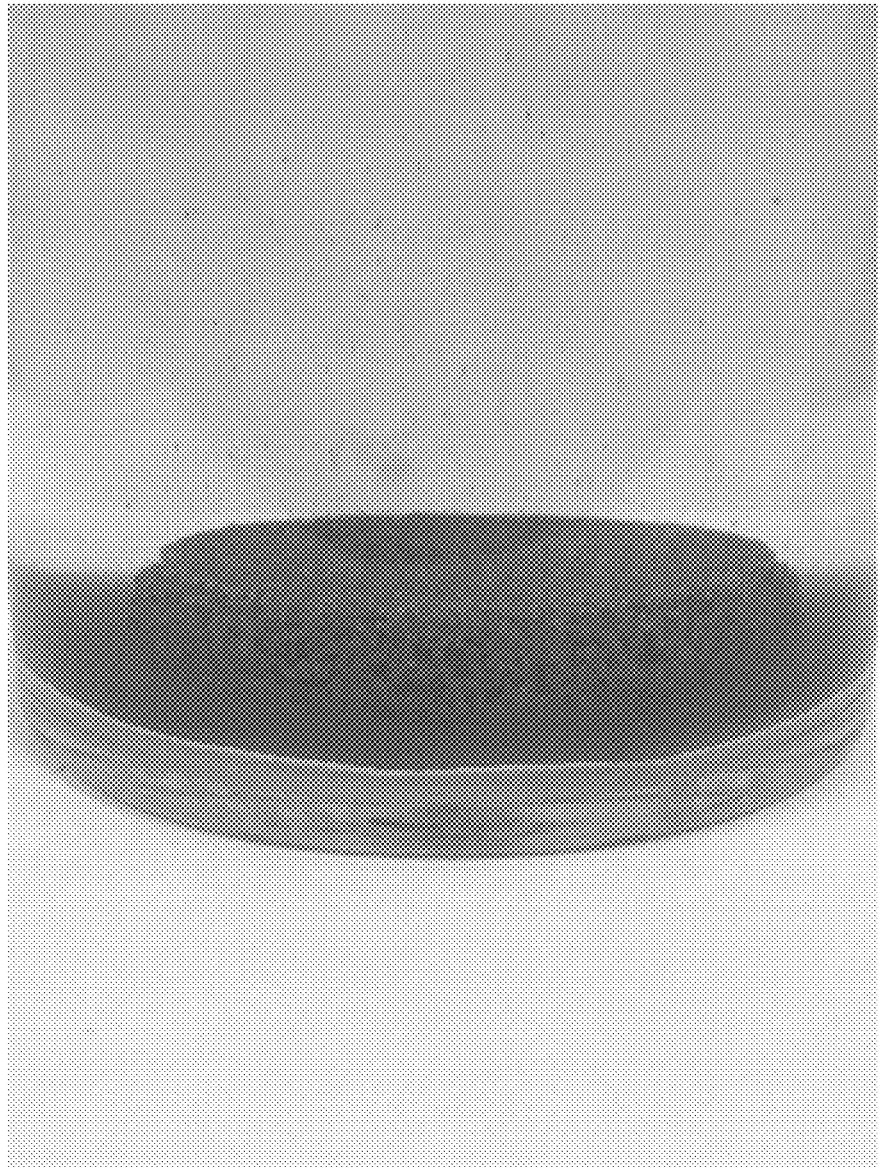

[Fig.5C]
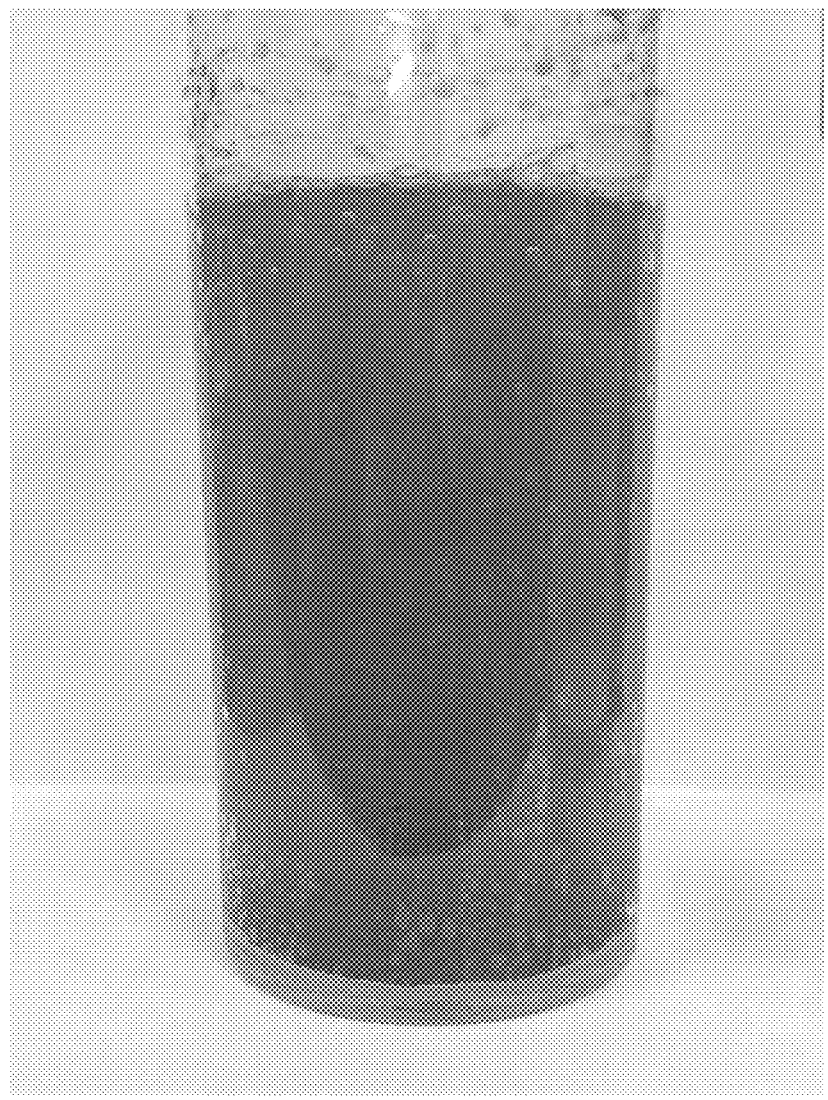

[Fig.6]
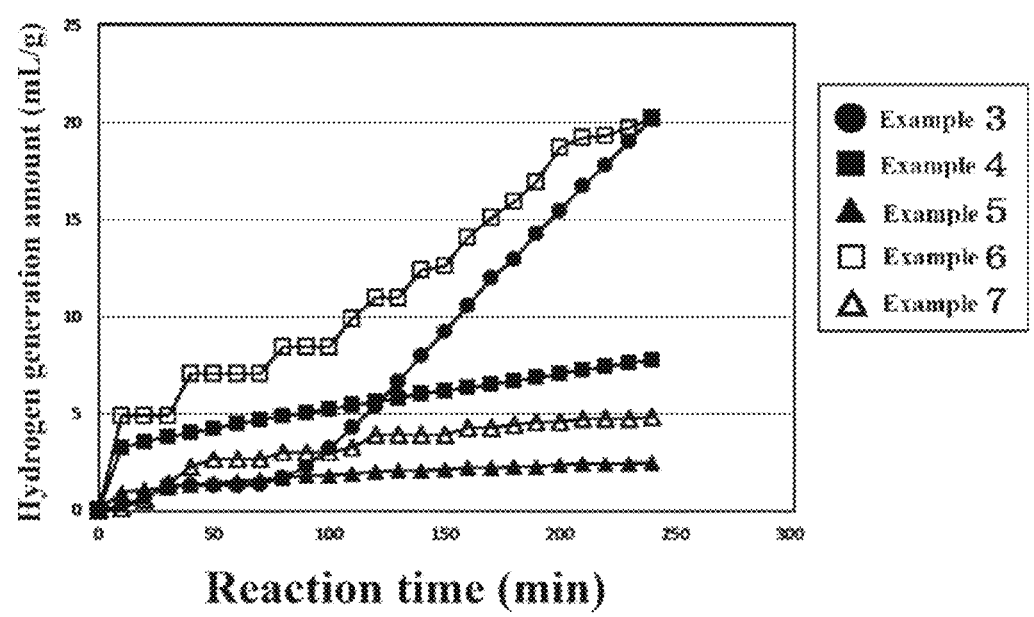

[Fig. 7]
(a)
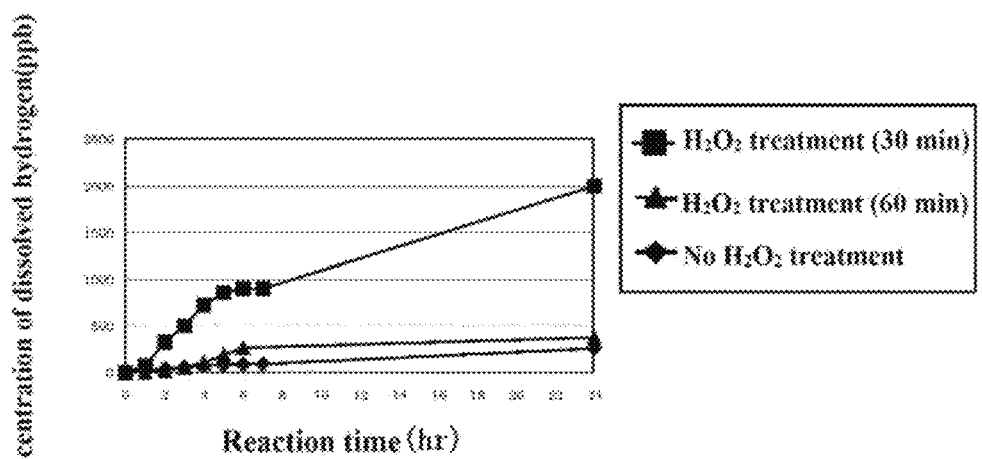
(b)
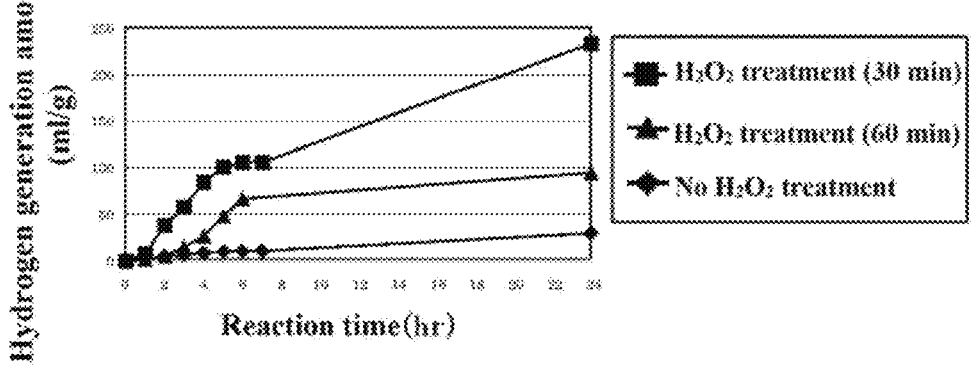

HYDROGEN SUPPLY MATERIAL AND PRODUCTION THEREFOR, AND HYDROGEN SUPPLY METHOD

CROSS-REFERENCE TO RELATED APPLICATION(S)

This application is a U.S. national stage entry of PCT Application No. PCT/JP2017/027173 filed Jul. 27, 2017, which claims the benefit of the earlier filing date of JP pplication No. JP 2016-162520 filed Aug. 23, 2016, both of which are incorporated herein by reference, in their entirety, for any purpose.

TECHNICAL FIELD

The present invention relates to a hydrogen supply material and a production method for the hydrogen supply material, and a hydrogen supply method.

BACKGROUND ART

Active oxygen derived from oxygen generated in the body and oxygen taken in from the lung is present in the body of an animal including a human. Active oxygen is known to oxidize and damage cells that form a living body while it is necessary for life support. For example, active oxygen, particularly a hydroxyl radical which has the strongest oxidizing power in active oxygen is considered to cause various diseases such as cancer, stroke, myocardial infarction, diabetes, other lifestyle diseases, and skin disorders such as skin aging and dermatitis. The hydroxyl radical is also said to adversely affect skin whitening or hair growth (including spots and dullness, or hair loss). Therefore, it is desirable that excess active oxygen, particularly the hydroxyl radical, which has not been used in a reaction useful for a living body, be prevented from being present in the body wherever possible.

Hydroxyl radicals produced in the body are eliminated by reacting with some substances. Hydrogen is known as one example of the substances that eliminate hydroxyl radicals. It is water that is produced by hydrogen reacting with hydroxyl radicals, and hydrogen does not produce substances harmful to a living body. Thus, a device for producing hydrogen water containing hydrogen which eliminates hydroxyl radicals in the body has been proposed (e.g. Patent Document 1).

The concentration of hydrogen in the hydrogen water, however, is as low as 1.6 ppm (saturated hydrogen concentration) at a maximum. Further, hydrogen in the hydrogen water is easily diffused into air to remarkably reduce the concentration of hydrogen with elapse of time. Therefore, a method of ingesting hydrogen water does not make it easy to lake in the body a sufficient amount of hydrogen for reacting with hydroxyl radicals in the body. Thus, for making it easy to take hydrogen in the body, a hydrogen-containing composition containing hydrogen and a surfactant has been proposed (Patent Document 2).

Meanwhile, the present inventors have researched decomposition of water and generation of hydrogen by silicon nanoparticles and the results of the research have been described (Non-Patent Document 1 and Patent Documents 3 and 4).

PRIOR ART DOCUMENTS

Patent Documents

Patent Document 1: Japanese Patent Publication No. 5514140

Patent Document 2: Japanese Patent Laid-open Publication No. 2015-113331

Patent Document 3: Japanese Patent Laid-open Publication No. 2016-155118

Patent Document 4: Japanese Patent Laid-open Publication No. 2017-104848

Non-Patent Document

Non-Patent Document 1: Shinsuke MATSUDA et al., Concentration of hydrogen molecules and splitting water using silicon nanoparticle, Extended Abstracts of the 62nd JSAP Spring Meeting, 2015, 11a-A27-6

SUMMARY OF THE INVENTION

Problems to Be Solved by the Invention

However, even when high-concentration hydrogen water is ingested, the amount of hydrogen contained in 1 liter of the hydrogen water is only 18 ml (milliliters) at a maximum in terms of gas, and further, much of hydrogen in the hydrogen water is gasified in the stomach and intestines. Thus, there is the problem of causing pnenmophagia (so-called "burp") because a sufficient amount of hydrogen is not necessarily taken in the body. On the other hand, when a hydrogen-containing composition with hydrogen encapsulated by a surfactant is ingested, it is necessary to ingest a large amount of the hydrogen-containing composition for taking a sufficient amount of hydrogen in the body. In addition, there can arise the above-described problem that hydrogen is released in the stomach.

Thus, the present inventors have focused on the fact that limiting the means of taking hydrogen in the body to conventional "drinking water" makes it difficult to take a necessary amount of hydrogen in the body for sufficiently reducing active oxygen. If it is possible to increase the opportunity of more naturally bringing the skin and/or the mucous membrane into contact with hydrogen in active scenes of human daily life (hereinafter, referred to collectively as "life scenes"), the total amount of hydrogen that can be taken in the body throughout the whole life scenes is significantly increased, even with the amount of hydrogen taken in the body limited in each of life scenes. The present inventors have considered that such an ingenious attempt is capable of making hydrogen reach or close to a sufficient amount for reaction with hydroxyl radicals in the body, and earnestly conducted research and development on the attempt.

Solutions to the Problems

The present invention solves at least one of the above-described technical problems and greatly contributes to making a sufficient amount of hydrogen easily be taken in the body for eliminating hydroxyl radicals in the body in life scenes.

As a result of repetitive earnest studies and analyses by the present inventors based on the above-described focusing points, the present inventors have obtained very interesting knowledge. Specifically, the present inventors have found that certain characteristic silicon fine particles or aggregates thereof hardly generate hydrogen even when brought into contact with a water-containing liquid having a pH value in a certain numerical range or a medium capable of containing the water-containing liquid, but the silicon fine particles or the aggregates thereof are capable of remarkably generating hydrogen when brought into contact with a water-containing liquid having a pH value in another numerical range or a medium capable of containing the water-containing liquid (hereinafter, also referred to collectively as a "medium"). In addition, the present inventors have also obtained knowledge that the hydrogen generation amount considerably increases as the pH value increases. The "water-containing liquid" in the present application includes water itself, human sweat, and human body fluid.

On the other hand, the present inventors have noted that the generation of hydrogen can be inhibited not only by the presence of the skin and or the mucous membrane itself but also by the presence of "sweat" that is unavoidable in life scenes when means other than oral ingestion is employed, in other words, when hydrogen is attempted to be taken in the body (including the skin itself or the mucous membrane itself) by bringing hydrogen into contact with the skin and/or the mucous membrane. The "skin" and the "sweat" sometimes show acidity (weak acidity) to basicity (weak basicity), so that beneficial means for making hydrogen taken in the body with high accuracy can be adjusting the pH environment of a human body site to be in contact with the silicon fine particles or the aggregates thereof in life scenes.

A hydrogen generation mechanism by a reaction of the silicon fine particles or the aggregates thereof with water molecules is represented by the following formula (Chemical Formula 1). As described above, however, the present inventors have found that the reaction represented by the formula (Chemical Formula 1) is a limited reaction when the silicon fine particles or the aggregates thereof are brought into contact with a medium having a low pH value (typically a pH value of less than 5) but the reaction proceeds when the silicon fine particles or the aggregates thereof are brought into contact with a medium having a pH value of 6 or more. Therefore, it has been very interestingly clarified that even a water-containing liquid that is weakly acidic and has a pH value of 6 (or a medium capable of containing the water-containing liquid) allows effective generation of hydrogen. The present inventors have found by further examination that in order to promote the generation of hydrogen, it is effective to bring the silicon fine particles or the aggregates thereof into contact with a medium having a pH value of more suitably 7 or more (or more than 7), further suitably more than 7.4 and with very suitably a medium that is basic (hereinafter, referred to as "alkaline") and has a pH value of more than 8.

$$Si+2H_2O \rightarrow SiO_2+2H_2 \quad \text{(Chemical Formula 1)}$$

On the basis of the above-described knowledge, the present inventors have found that it is possible to solve at least a part of the above-described technical problems by utilizing the silicon fine particles or the aggregates thereof as well as appropriately adjusting or setting the usage environment of the silicon fine particles or the aggregates thereof. The present invention has been made on the basis of the above-described point of view.

One hydrogen supply material according to the present invention includes silicon fine particles having a capability of generating hydrogen and aggregates of the silicon fine particles, and a physiologically acceptable medium that gets contact with the silicon fine particles or the aggregates thereof. The hydrogen supply material is a hydrogen supply material for bringing the hydrogen into contact with a skin and/or a mucous membrane through the medium.

The hydrogen supply material is capable of brining hydrogen into contact with the skin and/or the mucous membrane to allow the hydrogen to be taken in the body (including the skin itself or the mucous membrane itself) by means other than oral ingestion, the hydrogen being generated by bringing the physiologically acceptable medium into contact with the silicon fine particles or the aggregates thereof.

In the invention of the hydrogen supply material, one preferred aspect is that the hydrogen supply material further includes, for example, an impermeable film that covers a solid formulation/a solid material (hereinafter, referred to representatively as a "solid formulation") of the silicon fine particles or the aggregates thereof or that covers a layer including the silicon fine particles or the aggregates thereof, and the medium gets contact with the silicon fine particles when at least a part of the film is removed or dissolved, in terms of enabling selection of a scene in need of generation of hydrogen with a high degree of freedom.

One production method for a hydrogen supply material according to the present invention includes a contact step of bringing silicon fine particles having a capability of generating hydrogen or aggregates of the silicon fine particles into contact with a physiologically acceptable medium to bring the hydrogen into contact with a skin and/or a mucous membrane through the physiologically acceptable medium.

The production method for a hydrogen supply material provides an opportunity of bringing the hydrogen into contact with the skin and/or the mucous membrane through the physiologically acceptable medium, the hydrogen being generated by the contact step of bringing the medium into contact with the silicon fine particles or the aggregates thereof. As a result, the production method for a hydrogen supply material is capable of producing a hydrogen supply material that allows hydrogen to be taken in the body (including the skin itself or the mucous membrane itself) by means other than oral ingestion.

One hydrogen supply method according to the present invention includes a contact step of bringing silicon fine particles having a capability of generating hydrogen or aggregates of the silicon fine particles into contact with a physiologically acceptable medium to bring the hydrogen into contact with a skin and/or a mucous membrane through the physiologically acceptable medium.

The hydrogen supply method provides an opportunity of bringing the hydrogen into contact with the skin and/or the mucous membrane through the physiologically acceptable medium, the hydrogen being generated by the contact step of bringing the medium into contact with the silicon fine particles or the aggregates thereof. As a result, the hydrogen supply method allows hydrogen to be taken in the body (including the skin itself or the mucous membrane itself) by means other than oral ingestion.

Also in the invention of the production method for a hydrogen supply material or the invention of the hydrogen supply method, one preferred aspect is bringing the silicon fine particles into contact with the medium when at least a part of an impermeable film that covers a solid formulation of the silicon fine particles or the aggregates thereof or that covers a layer including the silicon fine particles or the aggregates thereof is removed or dissolved, in terms of enabling selection of a scene in need of generation of hydrogen with a high degree of freedom.

In the present application, the expression "crystallite" is employed rather than the expression "crystal grain (or crystal particle)" when the diameter of a crystal is in the "nm order." On the other hand, the expression "crystal grain (or crystal particle)" is employed when the diameter of a crystal is in the "μm order."

Here, the "silicon fine particles" in the present application include "silicon nanoparticles" having an average crystallite diameter in the nm order, specifically a crystallite diameter of 1 nm or more and 100 nm or less. In a narrower sense, the "silicon fine particles" in the present application include, as main particles, silicon nanoparticles having an average crystallite diameter at a nano level, specifically a crystallite diameter of 1 nm or more and 50 nm or less. Here, according to the present inventor, silicon nanoparticles having a main crystallite diameter of 1 nm or more and less than 10 nm are the "silicon fine particles" that attain the finest division as one employable aspect. In the present application, the silicon fine particles include not only individually dispersed silicon nanoparticles, but also silicon nanoparticles in a state of aggregates that are formed by natural gathering of a plurality of the silicon nanoparticles and have a size close to a μm size (generally 0.1 μm or more and 1 μm or less).

As described above, the "silicon fine particles" in the present application can be aggregated in a natural state to form aggregates having a diameter size at a μm level (e.g. about 1 μm). In the present application, a lump solid preparation that is obtained by artificially pulling the silicon fine particles together through addition of a binding agent, compression, or the like and has such a size to be picked up by human fingers is sometimes referred to as a "solid formulation" for discriminating the lump solid preparation from the "aggregates." Typical examples of the "solid formulation" include tablets, and granules and a powdered preparation which assume a powdery form rather than a lump form. The "silicon fine particles" or the "aggregates of the silicon fine particles" in the present application are capable of forming a layer or a film (hereinafter, referred to collectively as a "layer").

The "physiologically acceptable substance or material" in the present application is a substance or a material that is substantially innocuous and causes substantially no side effect or harmful reaction even when brought into contact with the skin or the mucous membrane. The term "physiologically" includes a "medical" meaning.

Effects of the Invention

The one hydrogen supply material according to the present invention is capable of brining hydrogen into contact with the skin and/or the mucous membrane to allow the hydrogen to be taken in the body (including the skin itself or the mucous membrane itself) by means other than oral ingestion, the hydrogen being generated by bringing the physiologically acceptable medium into contact with the silicon fine particles or the aggregates thereof.

The one production method for a hydrogen supply material according to the present invention is capable of producing a hydrogen supply material that allows hydrogen to be taken in the body (including the skin itself or the mucous membrane itself) by means other than oral ingestion.

The one hydrogen supply method according to the present invention allows hydrogen to be taken in the body (including the skin itself or the mucous membrane itself) by means other than oral ingestion.

BRIEF DESCRIPTION OF THE DRAWINGS

FIG. 1 shows photographs ((a) perspective view and (b) side view) of a solid formulation according to a first embodiment.

FIG. 2 shows a schematic diagram illustrating a state in which hydrogen generated by a contact step of the first embodiment is in contact with the skin and/or the mucous membrane of a human in a bath through a medium (bathwater).

FIG. 3A shows a side view (a) illustrating a laminate structure of a layered solid formulation and a medium before generation of hydrogen in a modified example (2) of the first embodiment, and a side view (b) of the laminate structure of the layered solid formulation and the medium when hydrogen is generated in the modified example (2) of the first embodiment.

FIG. 3B shows a side view illustrating a structure of a layered solid formulation in a modified example (3) of the first embodiment.

FIG. 4 shows a graph illustrating the amount of hydrogen generated in Examples 1 and 2.

FIG. 5A shows a photograph illustrating a stale of a solid formulation in accordance with the first embodiment directly after the solid formulation is brought into contact with pure water.

FIG. 5B shows a photograph illustrating a slate of the solid formulation in accordance with the first embodiment about 60 seconds after the solid formulation is brought into contact with pure water.

FIG. 5C shows a photograph illustrating a state of a solid formulation in accordance with a modified example (6) of the first embodiment directly after the solid formulation is brought into contact with pure water.

FIG. 6 shows a graph illustrating the hydrogen generation amount in Examples 3 to 7.

FIG. 7 shows a graph (a) illustrating chronological changes in amount of dissolved hydrogen generated by bringing silicon fine particles prepared under each condition of a second embodiment into contact with an aqueous solution obtained by dissolving sodium hydrogencarbonate in pure water, and a graph (b) illustrating chronological changes in hydrogen generation amount per 1 g of the silicon fine particles of the second embodiment.

DESCRIPTION OF REFERENCE SIGNS

20: Base
70: Film
90a: Bathwater
90b: Medium
100: Solid formulation
100a: Layered solid formulation
200: Laminate structure

EMBODIMENTS OF THE INVENTION

Embodiments of the present invention will be described in detail with reference to the accompanying drawings.

First Embodiment

A hydrogen supply material according to the present embodiment includes silicon fine particles having a capability of generating hydrogen (or aggregates of the silicon fine particles), and a medium that gels contact with the silicon fine particles (or the aggregates thereof). Hereinafter, silicon fine particles (or aggregates thereof) and a solid formulation containing the silicon fine particles (or the aggregates thereof) will be described in detail as one example of the hydrogen supply material according to the present embodiment. In addition, a production method for a hydrogen supply material and a hydrogen supply method according to the present embodiment will be also described in detail.

[1] Silicon Fine Particles (or Aggregates Thereof), or Solid Formulation, and Production Method for Silicon Fine Particles (or Aggregates Thereof) or Solid Formulation The solid formulation according to the present embodiment is produced using silicon fine particles (hereinafter, also referred to as "silicon nanoparticles" for the sake of convenience) including, as main particles, silicon nanoparticles obtained by finely dividing, according to a bead mill method, a commercially available high-purity silicon particle powder (typically, manufactured by Kojundo Chemical Laboratory Co., Ltd., particle diameter distribution; <φ5 μm (but silicon particles having a crystal grain diameter of more than 1 μm, purity: 99.9%, i-type silicon) as silicon particles. The present embodiment employs a step of grinding silicon particles in ethanol solution to form the silicon fine particles or aggregates of the silicon fine particles.

Specifically, 200 g of the high-purity silicon powder is dispersed in 4 L (litters) of a 99.5 wt % ethanol solution, φ0.5 μm zirconia beads (volume: 750 ml) are added, and the mixture is finely divided by performing grinding (one-step grinding) at a rotation speed of 2500 rpm for 4 hours using a bead mill apparatus (manufactured by AIMEX CO., Ltd. horizontal continuous ready mill, (model: RHM-08).

In the present embodiment, a separation slit provided in a grinding chamber of the bead mill apparatus separates the mixture into the beads and an ethanol solution containing silicon nanoparticles. The ethanol solution containing silicon nanoparticles that has been separated from the beads is heated to 30° C. to 35° C. with a vacuum evaporator. As a result, the ethanol solution is evaporated to give the silicon nanoparticles and or aggregates thereof.

The silicon fine particles obtained by the above-mentioned method mainly include silicon nanoparticles having a crystallite diameter of 1 nm or more and 100 nm or less. More specifically, as a result of measuring the silicon nanoparticles by an X-ray diffractometer (SmartLab manufactured by Rigaku Corporation), the following values were obtained as one example. In a volume distribution, the mode diameter was 6.6 nm, the median diameter was 14.0 nm, and the average crystallite diameter was 20.3 nm.

The silicon nanoparticles were observed using a scanning electron microscope (SEM), and the result showed that the silicon nanoparticles were partially aggregated to form slightly large formless aggregates with about 0.5 μm or less. In addition, individual silicon nanoparticles were observed using a transmission electron microscope (TEM), and the result showed that main silicon nanoparticles had a crystallite diameter of about 2 nm or more and 20 nm or less.

Thereafter, a first mixing step of mixing hydrogen peroxide water with the silicon nanoparticles in a glass container (hereinafter, also referred to as a "$H_2O_2$ treatment" or a "hydrogen peroxide water treatment step") is performed in the present embodiment. In the present embodiment, the temperature of the hydrogen peroxide water (3.5 wt % in the present embodiment) in the mixing step is 75° C. The mixing time is 30 minutes. Sufficient stir in the first mixing step (hydrogen peroxide water treatment step) is preferred to increase the opportunity of the silicon nanoparticles getting in contact with the hydrogen peroxide water. Even when the temperature of the hydrogen peroxide water in the first mixing step (hydrogen peroxide water treatment step) is, for example, about room temperature, at least a part of the effects of the present embodiment can be exhibited.

The silicon nanoparticles mixed with the hydrogen peroxide water are subjected to a solid-liquid separation treatment using a known centrifugal separator to remove the hydrogen peroxide water and thus give silicon nanoparticles. As a result, it is possible to obtain silicon nanoparticles having their surfaces treated with hydrogen peroxide water. Here, the treatment of the surfaces of the silicon nanoparticles with hydrogen peroxide water is capable of removing an alkyl group (e.g. a methyl group) present on the surfaces of the silicon nanoparticles. As a result, the silicon nanoparticles (and silicon fine particles including, as main particles, the silicon nanoparticles) and aggregates thereof are capable of forming a state in which they have surfaces capable of getting direct contact with a medium capable of containing a water-containing liquid, while as a whole retaining hydrophilicity on their surfaces. Such a special surface treatment is capable of promoting the generation of hydrogen with higher accuracy.

Thereafter, a second mixing step of mixing the silicon nanoparticles with an ethanol solution is further performed in the present embodiment. Sufficient stir in the mixing step is preferred to increase the opportunity of the silicon nanoparticles getting in contact with the ethanol solution (99.5 wt % in the present embodiment). The silicon nanoparticles mixed with the ethanol solution are subjected to a solid-liquid separation treatment using a known centrifugal separator for removal of the ethanol solution that is highly volatile and then sufficiently dried to produce one type of final silicon nanoparticles according to the present embodiment.

In the present embodiment, as another type of final silicon nanoparticles, silicon nanoparticles were also produced, with the mixing time of the hydrogen peroxide water with the silicon nanoparticles set to 60 minutes in the first mixing step of the above-described steps. Another aspect of the present embodiment also includes appropriate control of the shape and the structure of the silicon fine particles and the aggregates thereof.

The present embodiment does not use isopropyl alcohol unlike a second embodiment described later but uses the ethanol solution and the hydrogen peroxide water, and thus, it is worth noting that it is possible to provide a hydrogen supply material, a production method for a hydrogen supply material, and a hydrogen supply method that are safer and more secure for a living body.

Thereafter, 2 g of the produced silicon nanoparticles are mixed with 38 g of a sodium hydrogencarbonate powder (manufactured by Wako Pure Chemical Industries, Ltd., purity: 99.5%). The mixture is kneaded and formed into a substantially columnar lump body having a diameter of about 50 mm and a height of about 8 mm by a tableting method to give a solid formulation 100 shown in FIG. 1. FIG. 1(*a*) is a perspective view of the solid formulation 100 as one example, and FIG. 1(*b*) is a side view of the solid formulation 100 as the one example. One employable aspect is also an aspect in which the silicon fine particles or the aggregates thereof forming no solid formulation are contained in a known material forming, for example, a known bath additive.

[2] Medium and Production Method for Medium

Next prepared is a "medium" with which the silicon nanoparticles (or the aggregates thereof) or the solid formulation 100 is brought into contact.

A material or a commercial product for the "medium" in the present embodiment is not particularly limited. At least a part of the effects of the present embodiment can be exhibited as long as the medium allows hydrogen to be dermally or transmucosally taken in the body (including the skin itself or the mucous membrane itself) and is a physiologically acceptable medium.

A suitable example of the medium is at least one selected from the group consisting of a liquid form, a gel form, a cream form, a paste form, an emulsion form, and a mousse form, in terms of increasing the opportunity of the human body site getting contact with water (or a wafer-containing liquid) or a medium containing the water (or the water-containing liquid) (hereinafter, also referred to collectively as a "medium") in life scenes. Another suitable example of the medium is bathwater (suitably alkaline bathwater). Therefore, in one example of the present embodiment, production of the bathwater is a production method for a medium.

Thus, in the present embodiment, tap water is typically retained as the bathwater in a general bathtub (including a bathtub in a public bathhouse, a public bathtub, and an interior or exterior bathtub set up by a Japanese inn) as shown in FIG. 2. Before or after the retention of the bathwater, the solid formulation 100 is disposed or charged into the bathtub to bring the solid formulation 100 into contact with bathwater 90a as the medium and thus generate hydrogen ($H_2$). Therefore, the solid formulation 100 according to the present embodiment is employable as a so-called bath additive.

Typical bathwater as the medium of the present embodiment is clean water such as tap water. When the bathwater 90a such as hot spring water (including hot spring water having clean water added thereto) other than clean water is used and the bathwater 90a such as hot spring water has a pH value (e.g. a pH value of 6) larger than weak acidity, the bathwater comes to have a high pH value due to the presence of sodium hydrogencarbonate contained in the solid formulation 100 according to the present embodiment to satisfy the condition as the medium that allows easy generation of hydrogen ($H_2$). In other words, when the hot spring water or the like is acidic, many solid formulations 100 are required to be introduced or charged into the bathwater 90a to make the bathwater satisfy the condition as the medium that allows easy generation of hydrogen ($H_2$).

The solid formulation 100 according to the present embodiment contains sodium hydrogencarbonate. Therefore, even when the bathwater 90a is neutral or weakly acidic, the solid formulation 100 is introduced or charged into the bathwater as the medium to undergo a contact step of bringing the silicon fine particles or the aggregates thereof according to the present embodiment into contact with the medium. As a result, it is possible to change the bathwater 90a to a weakly acidic medium having a pH value of 6 or more, more suitably a basic medium having a pH value of more than 7 and thus to promote the generation of hydrogen ($H_2$).

Therefore, as shown in FIG. 2, it is possible to bring hydrogen ($H_2$) generated by the contact step into contact with the skin and/or the mucous membrane of a human in a bath through the bathwater 90a as the medium. As a result, the present embodiment allows hydrogen ($H_2$) to be taken in the human body (including the skin itself or the mucous membrane itself) by means other than oral ingestion.

As described above, in the present embodiment, the bathwater 90a is capable of containing a water-containing liquid having a pH value of 7 or more and is capable of playing a role as the physiologically acceptable medium. As a result, it is possible to bring hydrogen ($H_2$) into contact with the skin and/or the mucous membrane through the medium (bathwater 90a).

Meanwhile, even if the solid formulation according to the present embodiment contains no sodium hydrogencarbonate, bathwater having a pH value of 6 or more (a pH value of more suitably 7 or more (or more than 7), a pH value of further suitably more than 7.4, very suitably more than 8) is capable of satisfying the condition as the medium that allows easy generation of hydrogen ($H_2$).

Modified Example (1) of First Embodiment

In the production method for a hydrogen supply material and the hydrogen supply method according to the first embodiment, one preferred aspect is that the production method and the hydrogen supply method further include an introduction step of introducing a "pH adjusting agent" into the medium, for adjusting the pH value of the bathwater 90a in the first embodiment to make the bathwater satisfy the condition for easier generation of hydrogen, in other words, to make the pH value of the bathwater to fall within the numerical range for easier generation of hydrogen.

The sodium hydrogencarbonate in the first embodiment is one example of the "pH adjusting agent," but the "pH adjusting agent" is not limited to sodium hydrogencarbonate. Therefore, the material for the "pH adjusting agent" is not limited as long as it is a material (hereinafter, also referred to as a "weak acidic agent") capable of adjusting the medium to weak acidity, or a pH value of 6 or more, or it is a material (hereinafter, also referred to as an "alkaline agent") capable of adjusting the medium to alkaline, or a pH value of more suitably 7 or more (or more than 7) (more suitably more than 7.4, further suitably more than 8). A typical example of the weak acidic agent is at least one acid or a salt thereof selected from the group consisting of citric acid, gluconic acid, phthalic acid, fumaric acid, and lactic acid. A typical example of the alkaline agent is at least one selected from the group consisting of potassium carbonate, sodium carbonate, sodium hydrogencarbonate, sodium hydroxide, and potassium hydroxide. The most suitable alkaline agent is sodium hydrogencarbonate in terms of physiology. This is because sodium hydrogencarbonate is widely used as a food additive and has a plurality of advantages such as a pH value adjustment function required in the present embodiment and excellent safety and versatility.

Modified Example (2) of First Embodiment

As another modified example of the first embodiment, the solid formulation according to the first embodiment can be formed in layers to form a laminate structure 200 of a layered solid formulation and a medium. FIG. 3A(a) shows a side view illustrating the laminate structure 200 of the layered solid formulation and the medium before generation of hydrogen, and FIG. 3A(b) shows a side view illustrating the laminate structure 200 of the layered solid formulation and the medium when hydrogen is generated.

As shown in FIGS. 3A(a) and 3A(b), the laminate structure 200 includes at least a layered solid formulation 100a and a medium 90b on or above a base 20 (e.g. fiber, a natural resin, a synthetic resin, metal, a semiconductor, ceramics, or glass). Here, as already described, a suitable example of the medium 90b is a material that is physiologically acceptable and is at least one selected from the group consisting of a liquid form, a gel form, a cream form, a paste form, an emulsion form, and a mousse form. The base 20 is stretchable in one preferred aspect. The base 20 is not necessarily provided when the laminate structure 200 of the layered solid formulation and the medium can be held without particularly providing the base 20.

As shown in FIG. 3A(a), in a stage before generation of hydrogen, an impermeable film 70 is provided between the layered solid formulation 100a and the medium 90b so as not to allow the layered solid formulation 100a to get contact with the medium 90b. A film formed of a known impermeable material can be utilized as the film 70. For example, an example of the material for the impermeable film 70 is a polymer such as known polyethylene. As another example, one employable aspect is also use of a water-disintegrable and impermeable sheet disclosed in International Publication No. WO 2011/036992.

On the other hand, as shown in FIG. 3A(b), drawing the film 70 to the arrow direction at least partially brings the layered solid formulation 100a into direct contact with the medium 90b. As a result, the layered solid formulation 100a can get contact with the medium 90b capable of containing a water-containing liquid having a pH value of 7 or more to generate hydrogen in cooperation with the pH adjusting agent typified by sodium hydrogencarbonate.

The present embodiment forms the structure so that drawing the film 70 in the arrow direction (toward the left on the paper) brings the layered solid formulation 100a into direct contact with the medium 90b. The method of removing the film 70, however, is not particularly limited. For example, one employable aspect is formation of the structure so that the medium 90b is brought into contact with the silicon fine particles (the layered solid formulation 100a in the present embodiment) or the aggregates thereof when at least a part of the film 70 is removed or dissolved. As regards an example of the material for dissolving at least a part of the film 70, one employable aspect is also employment of a water-disintegrate and impermeable sheet disclosed in International Publication No. WO 2011/036992. Another employable aspect is also covering with the impermeable film 70 the solid formulation 100 according to the first embodiment in place of the layered solid formulation 100a in a stage before generation of hydrogen. When removal or dissolution of the film 70 at least partially brings the solid formulation 100 into direct contact with the medium 90b, the same effects as those in the layered solid formulation 100a can be exhibited.

When the medium is, for example, at least one selected from the group consisting of a liquid form, a gel form, a cream form, a paste form, an emulsion form, and a mousse form, the two layers (the layered solid formulation 100a and the medium 90b) shown in FIG. 3A(b) are considered not to possibly retain a state of being clearly separated from each other. Such a case increases the contact area between the layered solid formulation 100a and the medium 90b and is thus rather preferred in terms of promoting the generation of hydrogen with higher accuracy. One employable aspect is also that the medium contains a physiologically acceptable adhesive agent for. for example, attachment of the medium to a human body site.

Modified Example (3) of First Embodiment

As another modified example of the first embodiment, another employable aspect is also a layered solid formulation produced by forming the solid formulation according to the first embodiment in layers. A structure 200a as one example shown in FIG. 3B includes a layered solid formulation 100a on a base 20. The base 20 is not necessarily provided when the shape of the layered solid formulation can be held without particularly providing the base 20. The impermeable film 70 shown in the modified example (2) of the first embodiment may be provided so as to cover the layered solid formulation 100a, in terms of highly accurately avoiding contact with moisture in air.

As shown in FIG. 3B, one preferred aspect of the present embodiment is, for example, bringing the layered solid formulation 100a into contact with the human skin or mucous membrane and then into contact with moisture-containing sweat or body fluid from the skin or mucous membrane to generate hydrogen. Such a case also allows a human to take hydrogen in his body in the same manner as in the modified example (2) of the first embodiment. It is possible to supply, as the moisture, water (e.g. clean water) in place of the sweat or the body fluid by, for example, spraying before (e.g. directly before) using the layered solid formulation 100a.

It is worth noting that the structures or the laminate structures of the embodiments are employable structures in various "life scenes." For example, typical commercial products that can employ (possibly include) the medium are exemplified by the following items (1) to (4):

(1) one washing agent selected from the group consisting of face-wash, hair shampoo, body shampoo, liquid hand soap, and liquid body soap;

(2) one cosmetic material selected from the group consisting of beauty lotion (e.g. one containing hyaluronic acid), beauty essence, milky lotion, lotion, beauty cream (e.g. one containing collagen), foundation, a skin pack (including a skin pack containing gel (or a gelled agent), shaving cream, hair rinse, hair treatment, a hair conditioner, a hair cosmetic, adiaphoretic, and a cosmetic substance for UV protection;

(3) one therapeutic material selected from the group consisting of ointment and fomentation; and (4) one hygienic material selected from the group consisting of a water-absorbent resin, water-absorbent nonwoven fabric, water-absorbent fiber, water-absorbent felt, and water-absorbent gel (or gelled agent).

Here, the "hair cosmetic" includes hair dressing, hair oil, camellia oil, styling (material), setting (material), blowing (material), brushing (material), tic, hair stick, hair wax, hair foam, hair gel, pomade, hair cream, hair solid, hair lacquer, hair liquid, hair spray, and hair water. The "hygienic material" includes hygienic gloves, a head cover, a head band, a bed pad, a bed sheet, an incontinence article for adults, a sanitary product, a clothing item, a wound treatment product (including a wound covering material, tape, and a bandage), a disposable diaper including a diaper for adults and a diaper for infants, gauze, a gown, a hygienic tissue (including a wet towel, a face washing towel, a patch, a wet tissue, and a napkin), absorbent cotton, a cotton swab, adhesive-plaster, and surgical tape.

Modified Example (4) of First Embodiment

As another modified example of the first embodiment, 4 g of citric acid (manufactured by Wako Pure Chemical Industries. Ltd., purity: 99.5%) is further added to 2 g of the silicon nanoparticles and 34 g of the sodium hydrogencarbonate powder that are used in the first embodiment, and the mixture is kneaded to form a substantially columnar lump body having a diameter of about 50 mm and a height of about 8 mm, so that the same solid formulation as the solid formulation 100 shown in FIG. 1 can be obtained.

Modified Example (5) of First Embodiment

As another modified example of the first embodiment, a solid formulation is obtained by the same treatments as in the modified example (4) of the first embodiment except that the amounts of the sodium hydrogencarbonate powder and citric acid are changed to 19 g and 19 g, respectively. This solid formulation is the same substantially columnar solid formulation as the solid formulation 100 shown in FIG. 1 and has a diameter of about 50 mm and a height of about 8 mm. The mixing ratio among citric acid, sodium hydrogencarbonate, and the silicon nanoparticles can be appropriately changed.

Modified Example (6) of First Embodiment

In the present embodiment, the same high-purity silicon particle powder as that used in the first embodiment (typically, silicon particles having a crystal grain diameter of more than 1 μm) is ground in one step by the procedures described in the first embodiment. In the present embodiment, the φ0.5 μm zirconia beads (volume: 750 ml) used in the one-step grinding are automatically separated from a solution containing silicon nanoparticles in a bead mill grinding chamber. Further, φ0.3 μm zirconia beads (volume: 300 ml) are added to the solution containing silicon nanoparticles from which the beads have been separated, and the mixture is finely divided by performing grinding (two-step grinding) at a rotation speed of 2500 rpm for 4 hours.

The silicon nanoparticles including the beads are separated from the solution containing silicon nanoparticles as described above. The ethanol solution containing silicon nanoparticles that has been separated from the beads is heated to 40° C. using a vacuum evaporator in the same manner as in the first embodiment, so that the ethanol solution is evaporated to give the silicon nanoparticles.

Modified Example (7) of First Embodiment

Another employable aspect is also further providing a physiologically acceptable covering layer that covers the solid formulation 100 according to the first embodiment or the solid formulations described in the modified examples (4) and (5) of the first embodiment. For example, it is possible to employ a known enteric material hardly soluble in the stomach, which is a coating agent that covers the outermost layer of the solid formulation 100. An example of a physiologically acceptable covering layer applicable as a capsule preparation is a capsule which encapsulates the silicon fine particles or the aggregates thereof and is produced from a known enteric material hardly soluble in the stomach. When the solid formulation 100 is employed, a disintegrating agent may be further included. For the disintegrating agent, a known material is employable. In addition, a preferred example of a more suitable disintegrating agent is an organic acid, and the most suitable example is citric acid. Here, the organic acid can also function as a binding agent that brings the silicon nanoparticles into a lump form.

The temperature condition is not particularly limited for the water-containing liquid for generating hydrogen or the medium capable of containing the water-containing liquid in the embodiments. The temperature of the medium that allows the generation of hydrogen, however, is higher than 0° C. and 50° C. or lower. The water-containing liquid or the medium having a temperature of suitably 20° C. (more suitably 25° C.) or higher and 50° C. or lower promotes the reaction of generating hydrogen. Further, the water-containing liquid or the medium having a temperature of 35° C. or higher and 50° C. or lower promotes the generation of hydrogen with higher accuracy. An upper limit of the temperature of the water-containing liquid or the medium is not particularly limited as long as a human is not wound, specifically burned, for example.

EXAMPLES

Hereinafter, the embodiments will be described in more detail by way of examples, but the embodiments are not limited to these examples.

Example 1

The present inventors checked the state of generation of hydrogen without performing a tableting step by a tableting method, to evaluate silicon nanoparticles themselves. Specifically, an experiment was conducted as Example 1, using silicon nanoparticles subjected to the one-step grinding in the first embodiment.

The silicon nanoparticles described in the first embodiment in an amount of 10 mg and in a form of a powdered preparation (i.e. the silicon nanoparticles were not either mixed or kneaded with a sodium hydrogencarbonate powder) were poured into a glass bottle having a volume of 100 ml (borosilicate glass having a thickness of about 1 mm, LABORAN Screw Tubular Bottle manufactured by AS ONE Corporation). Tap water baying a pH value of 7.1 in an amount of 30 ml was poured into the glass bottle, the glass bottle was hermetically sealed under the temperature condition of a liquid temperature of 25° C., the concentration of hydrogen in the liquid in the glass bottle was measured, and the hydrogen generation amount was determined using the measured concentration of hydrogen. For measurement of the concentration of hydrogen, a portable dissolved hydrogen meter (Model. DH-35A manufactured by DKK-TOA CORPORATION) was used.

Example 2

Example 2 was conducted in the same manner as Example 1 except that 30 ml of tap water was poured and the temperature condition was changed to a liquid temperature of 37° C.

FIG. 4 shows the results of Examples 1 and 2. In FIG. 4, the abscissa represents the time (min) during which the solid formulation was kept in contact with the water-containing liquid, and the ordinate of the graph represents the hydrogen generation amount.

As shown in FIG. 4, the generation of hydrogen was confirmed even when nearly neutral water was brought into contact with the silicon nanoparticles described in the first embodiment. It was clarified that a high liquid temperature increases the hydrogen generation amount. Particularly, it was confirmed that when the liquid temperature is 37° C. close to human body temperature, the generation of hydrogen is attained in a shorter time and a great amount (1.5 ml/g or more) of hydrogen is continuously generated thereafter.

In addition to the results of Examples 1 and 2, the present inventors conducted the evaluations indicated in Example 3 and the following examples for the various solid formulations that were processed by a tableting method and are described in the first embodiment and the modified examples thereof.

Example 3

Employed as a sample for Example 3 was a solid formulation having one-fifth (φ10×1.6 mm, silicon nanoparticles: 16 mg, sodium hydrogencarbonate: 304 mg) the diameter and the height of one solid formulation 100 produced by the treatments described in the first embodiment.

The sample was placed in a stainless container having a volume of 60 ml. Pure water (pH value: 7.0) as an example of the water-containing liquid in an amount of 60 ml was poured into the stainless container to immerse the solid formulation in the pure water, and the liquid temperature was kept at 25° C. Under this condition, the glass bottle was hermetically sealed, the concentration of hydrogen in hydrogen water produced in the glass bottle was measured using the meter described in Example 1, and the hydrogen generation amount was determined.

The solid formulation gradually disintegrated its shape in the pure water with elapse of time. Sodium hydrogencarbonate was dissolved in the liquid with elapse of time after the solid formulation was brought into contact with the pure water, and the silicon nanoparticles were partially settled and left on the bottom of the container while almost uniformly diffused in the liquid. As a result, the solid formulation hardly retained its original shape and assumed a powdery form (or a fine powdery form; hereinafter, referred to collectively as a "powdery form") (hereinafter, a phenomenon in which the form of a solid formulation is disintegrated into a powdery form is referred to as "disintegration." Dissolution of a capsule of a capsule preparation encapsulating a powder also means that the form of a formulation is disintegrated, and exposure of a powder by dissolution of a capsule is also encompassed in "disintegration"). In this example, sodium hydrogencarbonate released with disintegration of the solid formulation was dissolved in water, and therefore the pH value of the water-containing liquid in the glass bottle increased to 8.3.

Example 4

Example 4 employed as a sample a solid formulation having one-fifth (φ10×1.6 mm, silicon nanoparticles: 16 mg, sodium hydrogencarbonate: 272 mg, citric acid: 32 mg) the diameter and the height of the solid formulation produced by the treatments described in the modified example (4) of the first embodiment. The solid formulation was almost wholly disintegrated into a powdery form about 5 minutes after brought into contact with pure water under the temperature condition of a liquid temperature of 25° C. In the process of disintegration of the solid formulation (i.e. until 90 minutes after the solid formulation was brought into contact with pure water), sodium hydrogencarbonate and citric acid were released with disintegration of the solid formulation, so that the water-containing liquid had a pH value of 7.6.

Example 5

Example 5 employed as a sample a solid formulation having one-fifth (φ10×1.6 mm, silicon nanoparticles: 16 mg, sodium hydrogencarbonate: 152 mg, citric acid: 152 mg) the diameter and the height of the solid formulation prepared by the procedures described as the modified example (5) of the first embodiment. The solid formulation was almost wholly disintegrated into a powdery form about 5 minutes after brought into contact with pure water under the temperature condition of a liquid temperature of 25° C. In the process of disintegration of the solid formulation (i.e. until 90 minutes after the solid formulation was brought into contact with pure water), sodium hydrogencarbonate and citric acid were released with disintegration of the solid formulation, so that the water-containing liquid had a pH value of 6.0.

Example 6

Example 6 employed as a sample a solid formulation having one-fifth (φ10×1.6 mm, silicon nanoparticles: 16 mg, sodium hydrogencarbonate: 272 mg, citric acid: 32 mg) the diameter and the height of the solid formulation prepared by the procedures described as the modified example (6) of the first embodiment. The stainless container was held in a thermostatic bath to keep the liquid temperature at 37° C. As the water-containing liquid, pure water having a pH value of 7.0 was used. The solid formulation was almost wholly disintegrated into a powdery form about 5 minutes after brought into contact with pure water. Sodium hydrogencarbonate and citric acid were released with disintegration of the solid formulation, so that the water-containing liquid had a pH value of 7.6.

Example 7

Example 7 employed as a sample a solid formulation having one-fifth (φ10×1.6 mm, silicon nanoparticles: 16 mg, sodium hydrogencarbonate: 152 mg, citric acid: 152 mg) the diameter and the height of the solid formulation produced by the treatments described in the modified example (7) of the first embodiment. The stainless container was held in a thermostatic bath to keep the liquid temperature at 37° C. As the water-containing liquid, pure water having a pH value of 7.0 was used. The solid formulation was almost wholly disintegrated into a powdery form about 5 minutes after brought into contact with pure water. Sodium hydrogencarbonate and citric acid were released with disintegration of the solid formulation, so that the water-containing liquid had a pH value of 6.0.

In the examples, it is possible to confirm by visual inspection how the solid formulation gradually disintegrates its shape in pure water with elapse of time. One example of how the solid formulation is disintegrated is shown by FIGS. 5A and 5B that are photographs illustrating how a solid formulation (an example in accordance with the first embodiment) formed using 2 g of the silicon nanoparticles and 38 g of sodium hydrogencarbonate behaves with elapse of time when charged into 500 ml of pure water. FIG. 5A illustrates the state of the solid formulation directly after the solid formulation was brought into contact with pure water. FIG. 5B illustrates the state of the solid formulation about 60 seconds after the solid formulation was brought into contact with pure water.

On the other hand, FIG. 5C shows a photograph illustrating the state of a solid formulation (an example in accordance with the modified example (6) of the first embodiment) formed using 2 g of the silicon nanoparticles, 19 g of sodium hydrogen carbonate, and 19 g of citric acid, directly after the solid formulation was brought into contact with pure water.

As shown by FIGS. 5A to 5C it was confirmed that when the solid formulation was brought into contact with pure water, sodium hydrogencarbonate was dissolved in the liquid with elapse of time, and the silicon nanoparticles were partially settled and left on the bottom of the container while almost uniformly diffused in the liquid.

FIG. 6 shows the results of Examples 3 to 7. In FIG. 6, the abscissa represents the time (min) during which the solid formulation was kept in contact with the water-containing liquid, and the ordinate of the graph represents the hydrogen generation amount.

In Example 3, the solid formulation disintegrated its form to release sodium hydrogencarbonate as shown in FIGS. 5A and 5B. The hydrogen generation amount increased with elapse of contact time between the solid formulation and the water-containing liquid as shown in FIG. 6.

In comparison of Example 3 with Example 5 and comparison of Example 4 with Example 6, the hydrogen generation amount increased under a temperature condition of 37° C. close to human body temperature. Specifically, it is worth noting that Examples 3 and 6 were confirmed to be capable of generating 20 ml/g or more of hydrogen in 240 minutes (four hours).

Further, in comparison of the results of Examples 1, 2, and 6 in which the silicon nanoparticles retaining a powdery form were brought into contact with the water-containing liquid, with the results of Examples 3 to 5 and 7 in which the silicon nanoparticles were used as a solid formulation, it was clarified that the silicon nanoparticles retaining a powdery form are capable of generating more hydrogen when brought into contact with the water-containing liquid, particularly until a certain time (e.g. one and a half hours) after the silicon nanoparticles are brought into contact with the water-containing liquid.

<Experiment of Measuring Amount of Hydrogen Generated by Contact between Silicon Nanoparticles and Medium>

The present inventors also checked chronological changes in amount of hydrogen generated by bringing the silicon fine particles (not the solid formulation) prepared under each condition of the present embodiment into contact with an aqueous solution obtained by dissolving sodium hydrogencarbonate in pure water.

Specifically, 11 mg of the silicon nanoparticles (first mixing step: 30 minutes) or 5 mg of the silicon nanoparticles (first mixing step: 60 minutes) are mixed in a glass container with an aqueous solution having sodium hydrogencarbonate (1.88 wt %) dissolved therein. The aqueous solution has a pH of about 8.3. Thereafter, the glass container was filled to its opening with the aqueous solution and covered with a lid so as not to allow entry of air for complete hermetic sealing.

The lid was made of polypropylene, but a multilayer filter of polyethylene and polypropylene was used as an inner lid to enable sufficient inhibition of transmission and leakage of generated hydrogen. Some time later after the hermetic sealing, the silicon fine particles prepared under each condition of the present embodiment are confirmed from their appearance and by visual inspection to have been evenly mixed in the whole aqueous solution.

FIG. 7(a) shows a graph illustrating chronological changes in concentration of dissolved hydrogen generated by bringing the silicon fine particles (not the solid formulation) prepared under each condition of the present embodiment into contact with an aqueous solution obtained by dissolving sodium hydrogencarbonate in pure water. FIG. 7(b) shows a graph illustrating chronological changes in hydrogen generation amount per 1 g of the silicon fine particles prepared under each condition. The graphs show for reference the results of using the silicon fine particles not subjected to the first mixing step. The amounts of dissolved hydrogen were measured using a portable dissolved hydrogen meter (manufactured by DKK-TOA CORPORATION, model: DH-35A).

As shown in FIGS. 7(a) and 7(b). it was clarified that the first mixing step promotes the generation of hydrogen. Particularly, as shown in FIG. 7(b), it is worth noting that the first mixing step is performed to continuously give a hydrogen generation amount of 40 ml or more in 2 hours after elapse of 2 hours from the start of generation of hydrogen. Meanwhile, the hydrogen generation amount of the silicon fine particles subjected to the first mixing step with a mixing time of 60 minutes is considered to be smaller than the hydrogen generation amount of the silicon fine particles with a mixing time of 30 minutes due to the difference in thickness of an oxide film on the surfaces of the silicon fine particles. That is, it is considered that the silicon fine particles subjected to the first mixing step with a mixing time of 60 minutes had a thicker oxide film to make their direct contact with the medium (aqueous solution) difficult and thus to inhibit the generation of hydrogen.

According to further research and analyses by the present inventors, the silicon fine particles can attain sufficient surface areas capable of getting direct contact with the medium, while appropriately retaining hydrophilicity of the surfaces thereof, when subjected to the first mixing step with a mixing time of more than 2 minutes and 50 minutes or less (more suitably 3 minutes or more and 40 minutes or less, further suitably 4 minutes or more and 30 minutes or less, most suitably 5 minutes or more and 20 minutes or less). As a result, the generation of hydrogen can be more accurately promoted with the mixing time fallen within the above range.

Second Embodiment

A hydrogen supply material according to the present embodiment includes, as in the first embodiment, silicon fine particles having a capability of generating hydrogen (or aggregates of the silicon fine particles) and a medium that gets contact with the silicon fine particles (or the aggregates thereof). The present embodiment is substantially the same as the first embodiment in regard to the hydrogen supply material, the production method for a hydrogen supply material, and the hydrogen supply method except that an isopropyl alcohol (IPA) solution is employed in place of the ethanol solution employed in the first embodiment, so that duplicate description can be omitted.

[1] Silicon Fine Particles (or Aggregates Thereof) and Solid Formulation, and Production Method for Silicon Fine Particles (or Aggregates Thereof) and Solid Formulation The silicon fine particles according to the present embodiment have a capability of generating hydrogen. A solid formulation according to the present embodiment is a solid formulation that contains the silicon fine particles and has a capability of generating hydrogen. For the solid formulation according to the present embodiment, silicon fine particles (hereinafter, also referred to as "silicon nanoparticles" for the sake of convenience) are used that include, as main particles, silicon nanoparticles obtained by finely dividing, according to a bead mill method, a commercially available high-purity silicon particle powder (typically, manufactured by Kojundo Chemical Laboratory Co., Ltd., particle diameter distribution: <φ5 μm, purity 99.9%, i-type silicon) as silicon particles. Aggregates of the silicon fine particles can also have a capability of generating hydrogen.

Specifically, 15 g of a high-purity Si powder is dispersed in 300 ml of 99% or more isopropyl alcohol IPA), φ0.5 μm zirconia beads (volume: 300 ml) are added, and the mixture is finely divided by performing grinding (one-step grinding) at a rotation speed of 2500 rpm for 4 hours using a bead mill apparatus (manufactured by AIMEX CO., Ltd.: RMB Batch-Type Ready Mill).

Using a stainless steel material filter (mesh: 0.35 mm) attached to a bead separation container (manufactured by AIMEX CO., Ltd.), the silicon nanoparticles including the beads are subjected to suction filtration to separate the beads from the silicon nanoparticles. Thereafter, the isopropyl alcohol (IPA) solution containing the silicon nanoparticles separated from the beads is heated to 30° C. to 35° C. using a vacuum evaporator, so that isopropyl alcohol (IPA) is evaporated to give the silicon nanoparticles and/or aggregates thereof.

The silicon nanoparticles obtained by the above-mentioned method mainly include, as in the first embodiment, silicon nanoparticles having a crystallite diameter of 1 nm or more and 100 nm or less. Main silicon nanoparticles have a crystallite diameter of about 2 nm or more and 20 nm or less as in the first embodiment.

Specifically, 15 g of a high-purity Si powder is dispersed in 300 ml of 99% or more isopropyl alcohol (IPA), φ0.5 μm zirconia beads (volume: 300 ml) are added, and the mixture is finely divided by performing grinding (one-step grinding) at a rotation speed of 2500 rpm for 4 hours using a bead mill apparatus (manufactured by AIMEX CO., Ltd.: RMB Batch-Type Ready Mill).

Using a stainless steel material filter (mesh: 0.35 mm) attached to a bead separation container (manufactured by AIMEX CO., Ltd.), the silicon nanoparticles including the beads are subjected to suction filtration to separate the beads from the silicon nanoparticles. The IPA solution containing the silicon nanoparticles separated from the beads is heated to 40° C. using a vacuum evaporator, so that IPA is evaporated to give the silicon nanoparticles and/or aggregates thereof.

As in the first embodiment, the silicon nanoparticles obtained by the above-mentioned method include, as a main component, silicon nanoparticles mainly having a crystallite diameter of 1 nm or more and 100 nm or less. Main silicon nanoparticles have a crystallite diameter of about 2 nm or more and 20 mm or less as in the first embodiment.

In the same manner as in the first embodiment, the first mixing step of mixing hydrogen peroxide water with the silicon nanoparticles in a glass container is performed thereafter also in the present embodiment. The treatment of the surfaces of the silicon nanoparticles with hydrogen peroxide water is capable of forming silicon nanoparticles having a relatively thin and heterogeneous/incomplete oxide film on the surfaces thereof. As a result, the silicon nanoparticles (and silicon fine particles including, as main particles, the silicon nanoparticles) and/or aggregates thereof are capable of forming a state in which they have surfaces capable of getting direct contact with a medium capable of containing a water-containing liquid, while as a whole retaining hydrophilicity on their surfaces. Such a special surface treatment is capable of promoting the generation of hydrogen with higher accuracy.

Thereafter, the silicon nanoparticles possibly having isopropyl alcohol (IPA) partially attached thereto are subjected to a solid-liquid separation treatment using a known centrifugal separator to remove isopropyl alcohol (IPA) with high accuracy and then sufficiently dried to produce one type of final silicon nanoparticles according to the present embodiment.

In the present embodiment, as another type of final silicon nanoparticles, silicon nanoparticles were also produced, with the mixing time of the hydrogen peroxide water with the silicon nanoparticles set to 60 minutes in the first mixing step of the above-described steps.

The silicon nanoparticles can be, in the same manner as in the first embodiment, mixed with a sodium hydrogencarbonate powder to give a mixture, which is kneaded and then subjected to a tableting method to give a solid formulation.

Thereafter, the amount of hydrogen generated by contact between the silicon nanoparticles and the medium was examined to give the same results as the results of the first embodiment shown in FIG. 4.

Other Embodiments

One aspect of the production method for silicon fine particles in the hydrogen supply material includes a step of finely dividing silicon particles having a crystal grain diameter of more than 1 μm by a physical grinding method to form silicon fine particles mainly having a crystallite diameter of 1 nm or more and 100 nm or less. A suitable example of the physical grinding method is a method of grinding silicon particles by a bead mill grinding method, a planetary ball mill grinding method, a shock wave grinding method, a jet mill grinding method, or a combination of two or more thereof. However, in terms of production costs or ease of production control, a particularly suitable example is only a bead mill grinding method or a grinding method including at least a bead mill grinding method. The exemplified solid formulations in the embodiments not only play a role as the hydrogen supply material but also play a role as a hydrogen generation material for a living body that enables safe generation of hydrogen in vivo or ex vivo (hydrogen supply material for a living body).

The embodiments employ, as a starting material, silicon particles i.e. a commercially available high-purity silicon panicle powder. The starting material, however, is not limited to such silicon particles. One preferred aspect is also employing, as the starting material, for example, silicon chips, silicon cutting scraps, or silicon polishing scraps (hereinafter, also referred to as "silicon chips etc." or "chips etc.") which are usually disposed of as wastes in cutting processing of silicon in a process for production of a silicon wafer to be used in semiconductor products such as a solar cell, in terms of attaining lower costs and/or giving finer silicon nanoparticles. The object of the "silicon fine particles" is not limited to crystalline silicon. For example, it is also possible to use, as the starting material in the embodiments, silicon particles obtained by finely dividing an amorphous silicon layer formed on a known substrate by a CVD method. It is also possible to use, as the starting material or the finally-formed silicon fine particles in the embodiments, amorphous or crystalline silicon particles somewhat directly produced by, for example, a CVD method, a laser method, or an arc-discharge method.

The disclosure of the embodiments or the examples is intended for describing the embodiments and is not intended for limiting the present invention. In addition, modified examples within the scope of the present invention, including other combinations of the embodiments and the examples, are also to be included in the scope of claims.

INDUSTRIAL APPLICABILITY

A hydrogen supply material and a production method for a hydrogen supply material, and a hydrogen supply method according to the present invention increase the opportunity of more naturally bringing the skin and/or the mucous membrane into contact with hydrogen in various life scenes and thus can he used in many industries including a medical industry, a beauty industry, and health industry.

What is claimed is:

1. A hydrogen supply material comprising:
   silicon fine particles or aggregates thereof capable of generating hydrogen; and
   a physiologically acceptable medium that gets contact with the silicon tine particles or the aggregates, wherein the silicon fine particles or the aggregates of the silicon fine particles have a heterogeneous or incomplete oxide film on surfaces of the silicon fine particles or the aggregates of the silicon fine particles, and the surfaces of the silicon fine particles or the aggregates retain hydrophilicity, the hydrogen supply material being for bringing the hydrogen into contact with a skin and/or a mucous membrane through the physiologically acceptable medium, wherein the physiologically acceptable medium has a pH more than 7.4, and wherein the physiologically acceptable medium is at least one selected from the group consisting of a gel form, a cream form, a paste form, an emulsion form, and a mousse form.

2. The hydrogen supply material according to claim 1, further comprising a film impermeable to water, wherein the film covers a solid formulation of the silicon fine particles or the aggregates thereof, or covers a layer including the silicon fine particles or the aggregates thereof, wherein the physiologically acceptable medium is brought into contact with the silicon fine particles when at least a part of the impermeable film is removed or dissolved.

3. The hydrogen supply material according to claim 1, wherein the physiologically acceptable medium further contains at least one selected from the group consisting of potassium carbonate, sodium carbonate, sodium hydrogencarbonate, sodium hydroxide, and potassium hydroxide.

4. A washing agent, a cosmetic material, a therapeutic material, or a hygienic material comprising the hydrogen supply material according to claim 1.

5. The hydrogen supply material according to claim 1, wherein the silicon fine particles are substantially free of surface alkyl groups.

6. The hydrogen supply material according to claim 1, wherein the physiologically acceptable medium has a pH more than 8.

* * * * *